US00PP08677P

United States Patent [19]

Austin

[11] Patent Number: Plant 8,677

[45] Date of Patent: Apr. 12, 1994

[54] ROSE PLANT AUSBLOOM

[75] Inventor: David C. H. Austin, Albrighton, England

[73] Assignee: David Austin Roses Limited, Albrighton, England

[21] Appl. No.: 954,885

[22] Filed: Sep. 30, 1992

[51] Int. Cl.[5] ..... A01H 5/00

[52] U.S. Cl. ..... Plt./1

[58] Field of Search ..... Plt. 1, 29

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A shrub rose variety having bushy growth, large open deep red flowers, floriferousness, and moderate fragrance.

1 Drawing Sheet

The present invention relates to a new and distinct variety of shrub rose plant of the Rosa hybrida class which was originated by me by crossing the variety Mary Rose, with the variety Prospero.

The primary objective of this breeding was to produce a new rose variety having quartered, red, scented flowers on a bushy plant which repeatedly flowers. The objective was substantially achieved along with other desirable improvements as evidenced by the following unique combination of characteristics which are outstanding in the new variety and which distinguish it from its parents, as well as from all other varieties of which I am aware:

1. Large open deep red flowers;
2. Floriferousness;
3. Strong fragrance; and
4. Bushy plant.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Colour, except where ordinary dictionary significance of color is indicated.

Parentage:

*Seed parent.*—Mary Rose.

*Pollen parent.*—Prospero.

Classification:

*Botanical.*—Rosa hybrida.

*Commercial.*—Shrub.

FLOWER

Observations made from specimens grown in a garden environment in Albrighton, Wolverhampton, England, in Aug. 1991.

Blooming habit: Recurrent.

Bud:

*Size.*—About 1¼" long when the petals start to unfurl.

*Form.*—The bud form is long, apex pointed, globular.

*Color.*—When sepals first divide, the bud color is ruby 12D8. When half brown, the upper sides of the petals are Cerise 12C8; and the lower sides of the petals are Greyish rose 12B3.

*Sepals.*—Color: Grass green 30E7 with blush of violet brown 10E8. Surface texture: Dull, leathery. There are three normally appendaged sepals. There are two unappendaged sepals with hairy edges.

*Receptacle.*—Color: Deep green 29E8. Shape: Cup shaped. Size: Medium, about 1"×½". Surface: Smooth.

*Peduncle.*—Length: Medium, averaging about 2-2½". Surface: Smooth, glandular. Color: Bronzy (very faint blush). Strength: Erect.

Bloom:

*Size.*—Medium. Average open size is about 3-3½" in diameter.

*Borne.*—Singly, several together, in clusters of irregular shape of up to six flowers, very variable numbers of flowers/stems.

*Stems.*—Medium. Average length is about 12 to 18 inches.

*form.*—When first open: Cupped. Permanence: Flattens, outer petal edges curl slightly.

*Petalage.*—Number of petals under normal conditions: 140.

*Color.*—The upper side of the petals is 12C8 but more red, brighter. The reverse side of the petals is Greyish ruby 12C7. The base of the petals has a white basal tip deepening to yellow 3A7. The major color on the upper side is Cerise 12C8.

*Variegations.*—None.

*Discoloration.*—The general tonality at the end of the first day: a slight greying. At the end of the third day, the color of most of the petals is Greyish magenta 13D7, fading to greyish magenta 13D5.

*Fragrance.*—Moderate.

Petals:

*Texture.*—Thin, silky.

*Shape.*—Deltoid, heart-shaped, apex retuse.

*Form.*—Tips slightly recurved.

*Arrangement.*—Imbricated, with few petaloids in the center. Inner petals caught into space between perigynous zone and styles to form a button.

*Persistence.*—Petals drop off cleanly before drying.

*Lastingness.*—On the plant: About 7 to 10 days. As a cut flower: Fair, about 5 to 7 days.

Reproductive parts:

*Anthers.*—Size: Medium. Quantity: Many (70 to 75). Color: Reddish yellow 4A7. Arrangement: Tucked in calyx or partly so.

*Filaments.*—Color: Reddish yellow 4A7 with Cerise 12C8 blush.

*Pollen.*—Color: Good yellow.

*Styles.*—Color: Yellowish white 1A2, apex Cerise 12C8.

*Stigmas.*—Color: White, light yellow 4A5.

Form: Shrub.

Growth: Medium, branching bushy.

Height: 36 to 42.

Foliage: Number of leaflets on normal mid-stem leaves: 5.

*Size.*—About 1½" long×1" wide.

Quantity.—Normal.

*Color.*—New foliage: Dark green 30F7. Old foliage: Dark green 30F4/5.

Leaflets:

*Shape.*—Pointed oval, with round base.

*Texture.*—Upper side: Leathery.

*Edge.*—Serrated.

*Serration.*—Double, small.

*Petiole rachis.*—Color: Green.

*Petiole underside.*—With prickles, 1 to 3 per internode.

*Stipules.*—Medium, about 1–1¼" long.

*Disease resistance.*—Resistant to mildew and blackspot under normal growing conditions atr Albrighton, Wolverhampton, England.

Wood:

*New wood.*—Color: Light green (parrot green 30E8). Bark: Smooth.

*Old wood.*—Color: Green (Dark green 30F7). Bark: Smooth.

Prickles:

*Quantity.*—On main canes from base: Many to ordinary. On laterals from main canes: Ordinary.

*Form.*—Medium, hooked downward.

*Color when young.*—Green and red.

*Position.*—Evenly distributed.

Small prickles:

*Quantity.*—On main stalks: Few. On laterals: Few.

*Color.*—Brown.

I claim:

1. A new and distinct variety of shrub rose plant of the Rosa hybrida class, substantially as herein shown and described, characterized particularly as to novelty by the unique combination of its large open deep red flowers, floriferousness, and moderate fragrance.

* * * * *

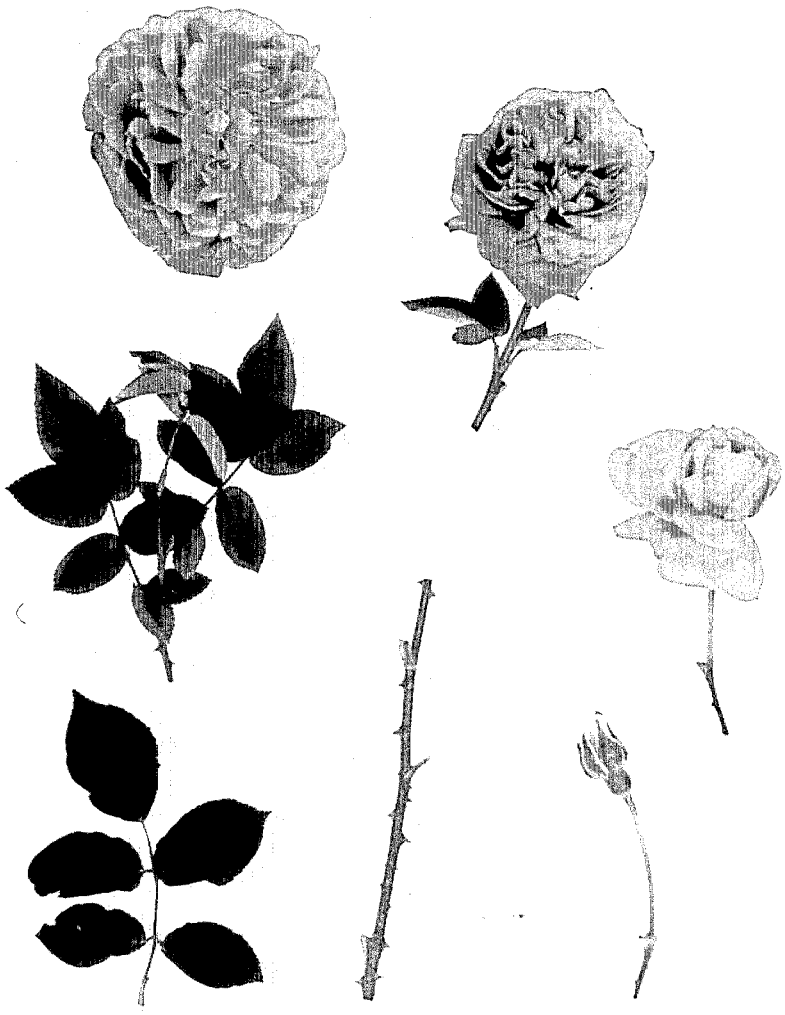

UNITED STATES PATENT AND TRADEMARK OFFICE

CERTIFICATE OF CORRECTION

PATENT NO. : PP 8,677

DATED : April 12, 1994

INVENTOR(S) : David Charles Henshaw Austin

It is certified that error appears in the above-identified patent and that said Letters Patent is hereby corrected as shown below:

Column 3, line 14, "Good Yellow" should be --Gold Yellow--; and

Column 4, line 7, "atr" should be --at--.

Signed and Sealed this

Eighth Day of November, 1994

Bruce Lehman

*Attest:*

BRUCE LEHMAN

*Attesting Officer*

*Commissioner of Patents and Trademarks*